United States Patent [19]
Coy et al.

[11] Patent Number: 4,755,355
[45] Date of Patent: Jul. 5, 1988

[54] TRACE LEVEL OXYGEN DETECTOR FOR ANAEROBIC ATMOSPHERES

[75] Inventors: Richard A. Coy, Grass Lake; Roy A. Waycaster, Tecumseh, both of Mich.

[73] Assignee: Coy Laboratory Products, Inc., Ann Arbor, Mich.

[21] Appl. No.: 883,268

[22] Filed: Jul. 8, 1986

[51] Int. Cl.[4] ............................................. G01N 27/12
[52] U.S. Cl. ...................... 422/96; 435/801; 435/807; 422/98; 436/147
[58] Field of Search .................. 422/83, 94, 95, 97, 422/98, 96; 435/801, 807; 436/147

[56] References Cited

U.S. PATENT DOCUMENTS

| | | | |
|---|---|---|---|
| 3,488,155 | 1/1970 | Ayers | 436/147 |
| 4,063,898 | 12/1977 | Fisher | 422/94 |
| 4,170,455 | 10/1979 | Henrie | 422/98 |
| 4,347,222 | 8/1982 | Beall et al. | 435/801 |
| 4,377,554 | 3/1983 | Johnson | 435/801 |
| 4,533,520 | 8/1985 | Bossart et al. | 422/98 |
| 4,579,631 | 4/1986 | Ishikawa et al. | 435/807 |
| 4,583,937 | 4/1986 | Yamana | 422/98 |

FOREIGN PATENT DOCUMENTS 0800192  1/1981  U.S.S.R. ............................. 435/801

*Primary Examiner*—Michael S. Marcus
*Attorney, Agent, or Firm*—Harness, Dickey & Pierce

[57] ABSTRACT

An oxygen detector for detecting the presence of trace levels of oxygen in an anaerobic environment consisting of a sample chamber wherein a sample from the anaerobic environment is exposed to a catalyst, such as palladium, which promotes the exothermic chemical reaction of oxygen with hydrogen. The presence of oxygen will cause such reaction to occur on the catalyst and the consequent generation of heat. A thermistor which is in thermal proximity to the catalyst detects this heat and provides a signal. The sampling chamber is enclosed by an enclosure which serves to volumetrically and thermally confine the sample during the measurement thereby enabling small levels of exothermic heat of reaction to be detected. Entrance to the sampling chamber is through a membrane which is permeable to lower molecular weight gases such as oxygen and hydrogen which thus enables diffusion of the anaerobic atmosphere into the chamber.

8 Claims, 2 Drawing Sheets

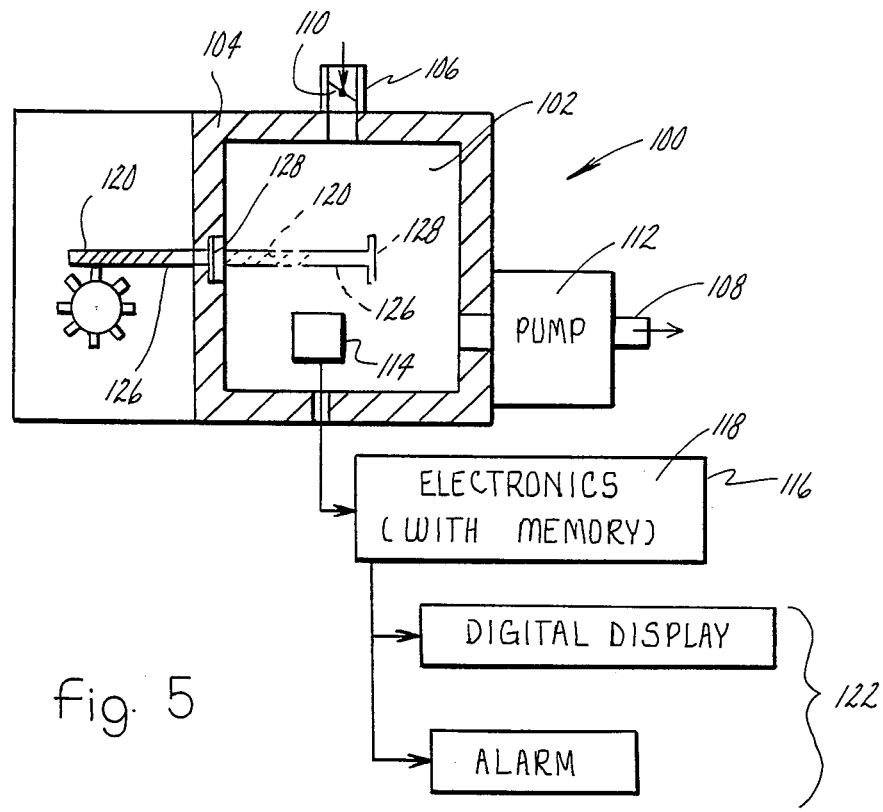
fig. 5
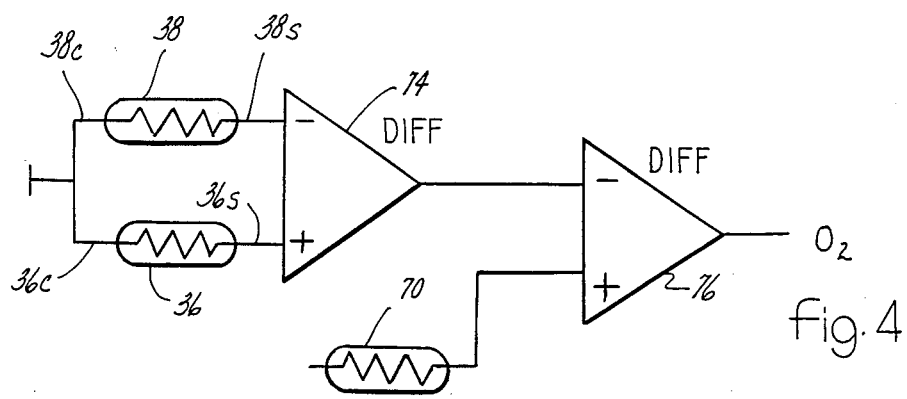
fig. 4
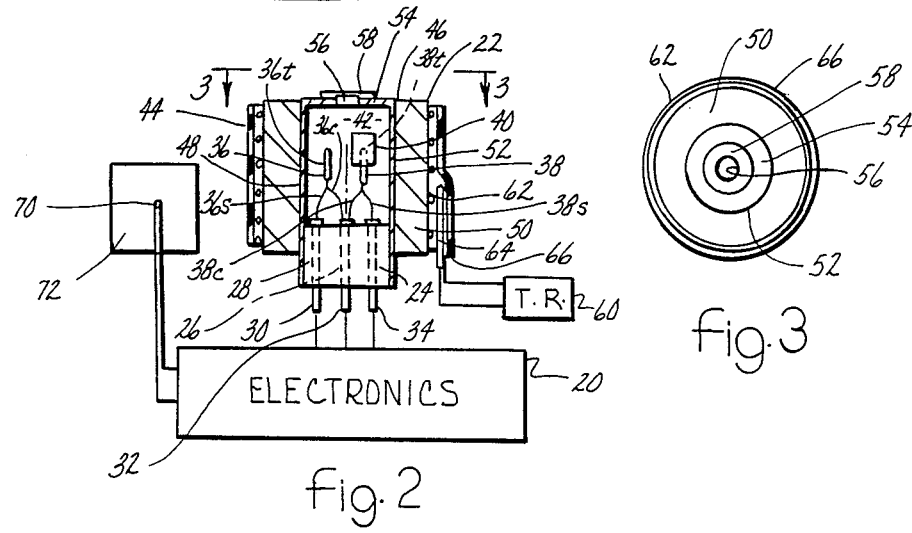
fig. 3
fig. 2

TRACE LEVEL OXYGEN DETECTOR FOR ANAEROBIC ATMOSPHERES

BACKGROUND AND SUMMARY OF THE INVENTION

This invention relates to an improvement in apparatus for detecting the presence of oxygen in an anaerobic environment, such as an anaerobic chamber.

A typical use for an anaerobic chamber is in the culturing of strict anaerobes. Various apparatus and pieces of equipment are contained within the enclosure for use in anaerobe culture. The enclosure is typically transparent, clear vinyl plastic for example, and work gloves for use by attending personnel are mounted in the wall of the enclosure. The personnel perform various work tasks within the enclosure via use of the flexible work gloves. The atmosphere within the enclosure is controlled by certain associated equipment and supply gases. Physical access to and from the interior of the enclosure is provided by an entry lock mechanism.

The presence of oxygen, even in minute amounts, can be disruptive to the anaerobic culturing process. Accordingly, anaerobic chambers may include catalyst boxes containing catalysts which are effective to aid in removal of stray oxygen from the chamber atmosphere.

As an aid to the use of an anaerobic chamber it is desirable to have an indicator of the presence of oxygen even though provisions exist for its removal. Because minute amounts of oxygen can potentially have undesired effects on anaerobic culture, it is important to be able to detect trace amounts of oxygen in an anaerobic chamber. While there are a number of commercially available oxygen detectors many of them do not possess a sufficiently high degree of sensitivity to detect trace levels. Other types of sensors which can detect trace levels are rather expensive.

There are known methods for detection of oxygen including: electrical conductivity; electrochemical cells; heat of reaction; paramagnetic analyzers; and thermomagnetic analyzers. Briefly, the electrical conductivity method involves the use of dissolved oxygen; the electrochemical cell method involves a polargraphic oxygen electrode; the heat of reaction method involves the detection of heat which occurs when oxygen and hydrogen combine and typically involves the use of a catalyst, such as palladium, to promote that action; the paramagnetic analyzer method involves the attraction of oxygen into a magnetic field; and the thermomagnetic analyzer method involves the use of heat and the paramagnetic property of oxygen. There is also a zirconium oxide analyzer which involves the use of oxygen concentration on a hot yttria tube and a measurement of differential voltage across the tube wall with a known concentration of oxygen on the inside of the tube.

The present invention relates to a trace level oxygen sensor for anaerobic environments which utilizes the heat of reaction method for detecting oxygen. It provides a number of significant advantages over other oxygen detectors, particularly for use in anaerobic environments. Several embodiments of the generic invention are disclosed. A specific preferred embodiment of the invention comprises a unique organization and arrangement which lends itself to fabrication at a cost which is a significant savings over other types of detectors for use in detecting trace levels of oxygen in an anaerobic chamber adapted for the culture of strict anaerobes. This preferred embodiment of the invention is compact and lends itself to being disposed in any desired position in the anaerobic environment and then connected by means of electrical wires to associated electronic equipment which provides information in a useful form for indicating when oxygen is present in an amount of a trace level. This preferred embodiment of the invention comprises a unique selection, organization, and arrangement of component parts in a compact assembly which does not require any significant modification of the anaerobic chamber except to provide for the wiring connection of the device to the associated electronic equipment which is typically located exterior of the chamber.

The foregoing features, advantages, and benefits of the invention, along with additional ones, will be seen in the ensuing description and claims which should be considered in conjunction with the accompanying drawings. The drawings disclose a preferred embodiment of the invention according to the best mode contemplated at the present time in carrying out the invention.

BRIEF DESCRIPTION OF THE DRAWINGS

FIG. 2 is a semi-schematic view partly in section of a trace oxygen detector embodying principles of the present invention.

FIG. 3 is a view of a portion of FIG. 2 taken generally in the direction of arrows 2—2.

FIG. 4 is a schematic electrical diagram illustrating further detail of a portion of FIG. 2.

FIG. 5 is a semi-schematic illustration of another embodiment of trace oxygen detector embodying principles of the present invention.

DESCRIPTION OF THE PREFERRED EMBODIMENT

Figure 1:
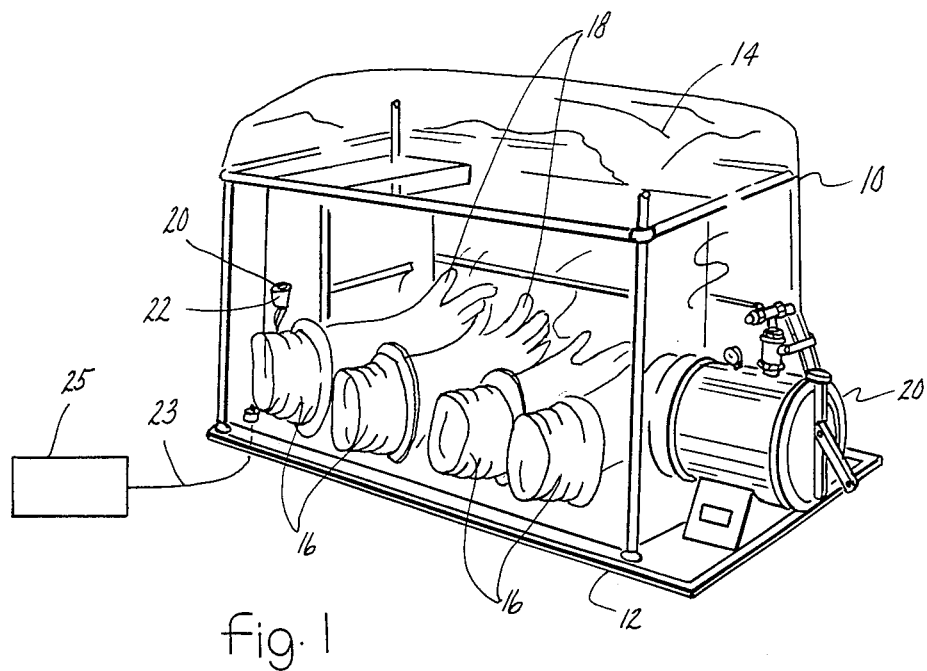
FIG. 1 is a perspective view of a typical anaerobic chamber with which the present invention is used.

FIG. 1 shows a representative anaerobic chamber 10 with which the present invention is used. Anaerobic chamber 10 comprises a horizontal base 12 on which is supported a transparent enclosure 14. The anaerobic atmosphere is within enclosure 14 and various apparatus and pieces of equipment are located within enclosure 14. The various apparatus and pieces of equipment may be manipulated by attending personnel via the personnel inserting their hands through cuffs 16 and into flexible gloves 18 which are mounted in the enclosure's wall. An entry lock mechanism, generally 20, is associated with enclosure 14 to provide for a physical introduction and removal of articles and gases into and out of the interior of enclosure 14. The anaerobic chamber need not be described in any further detail since such chambers are in commercial use, but so that trace oxygen can be detected, the anaerobic atmosphere is provided with a sufficient level of hydrogen.

Such uses can be adversely affected by the presence of even small trace amounts of oxygen. For example, in the culturing of strict anaerobes, trace oxygen can adversely effect the culturing process. Accordingly, in order to indicate the presence of a trace level of oxygen within the anaerobic atmosphere a trace detector 20 embodying principles of the present invention is cooperatively associated with anaerobic chamber 10. The detector comprises a sensing part 22 disposed within enclosure 14. Certain components of part 22 are electric circuit elements, and they are connected via suitable wiring, 23 generally, which extends from the enclosure to associated electronic apparatus 25 which is located externally of the enclosure.

FIGS. 2, 3, and 4 illustrate detail of detector 20. Part 22 is shown in representative detail in FIGS. 2 and 3. The illustrated embodiment is of generally circular cylindrical shape which affords certain advantages for fabrication. Principles however may be embodied in other than such a shape.

Sensing part 22 comprises a circular base 24 of the type commonly used in electrical connectors. The axis is designated 26. The base 24 has a non-metallic body 28 which is an electrical insulator. A series of metal conductor terminal pins extend through body 28 in a parallel manner parallel to the axis 26. In the illustrated base there are four such pins arranged at 90° intervals about axis 26 but only three of the pins are actually used for making electrical circuit connections in this particular embodiment. For convenience in explanation, the three pins used are identified by the reference numerals 30, 32, and 34.

Part 22 further comprises two thermistors 36, 38 which are supported by their own leads on base 24. Each thermistor 36, 38 has two leads. For thermistor 36 the leads are designated 36c and 36s and for thermistor 38, 38c and 38s. The two leads 36c, 38c are in common and connect to terminal pin 32 at the upper end face of insulator body 28 as viewed in FIG. 2. Lead 36s connects to pin terminal 30 and lead 38s to terminal pin 34. The sensing tip 36t of thermistor 36 is disposed in space. The sensing tip of thermistor 38 is disposed within a thimble shaped catalytic pellet 40. Pellet 40, has a circular cylindrical shape with a central blind hole extending axially from one end. It is within this hole that the sensing tip of thermistor 38 is disposed.

The catalytic pellet 40 is of a material which promotes an exothermic chemical reaction of oxygen with hydrogen and in the illustrated example the use of palladium is an effective catalyst for promoting the exothermic reaction of free oxygen gas with hydrogen gas to form water. Hence trace oxygen which may be present within the anaerobic chamber's interior will produce such a reaction on the palladium pellet when oxygen is present in the anaerobic environment.

The sensing tips of the two thermistors 36, 38 and the palladium pellet 40 are disposed within a sampling space 42 which is defined by part 22. This sampling space is bounded at one axial end by base 24. The side of the sampling space are bounded by a tubular sidewall structure 44. An endwall structure 46 axially bound the other end opposite base 28. Details of these further side and end wall structures will be subsequently explained. The enclosure formed by the side and end wall structures forms a sampling space which is confined both volumetrically and thermally. The nature of the confinement enables the exothermic reaction of oxygen with hydrogen on pellet 40 to be detected even for trace amounts of oxygen.

The material of base 28 is one which is a reasonably good thermal insulator, so that it possesses considerable thermal inertia. A tubular walled mass of large thermal inertia is used to form the sidewall structure 44. This structure comprises a thin walled aluminum sleeve 48 having an open end fitted onto base 24 surrounded by a much thicker brass tube 50. There is preferably a thin film 52 of suitable material between the two dissimilar metals. The aluminum sleeve includes an end wall 54 with a small central aperture 56. The aperture 56 is covered by a membrane 58 of a material which is permeable to lower molecular weight gases such as oxygen and hydrogen and permitting diffusion of the anaerobic atmosphere into the sampling space.

While the construction so far described defines a sampling space 42 which is substantially confined both volumetrically and thermally, it is desirable to have temperature of the structure bounding the sampling space regulated to a desired level. This is done by a temperature regulator system 60 which is cooperatively associated with part 22. The illustrated embodiment of system 60 comprises a thin film heater assembly 62 wrapped circumferentially around the outside of tube 50. A temperature sensor 64 is disposed against heater assembly 62 and both heater 62 and sensor 64 are held in place by a suitable wrap 66 such as thermal electrical tape. The heater 62 and sensor 64 are cooperatively associated by wires in electric circuit with an electrical power supply whereby suitable current is delivered from the supply to the heater 62 to maintain a desired regulated temperature.

In the preferred embodiment of the invention a third temperature sensor in the form of a thermistor 70 is disposed to sense the ambient temperature of the anaerobic atmosphere at a location spaced from sensing part 22. In order to avoid momentary fluctuations the sensing tip of thermistor 70 is disposed in contact with a thermal mass 72 at a suitable location within the enclosure.

Wires serve to connect these various electrical components with the associated electronic apparatus which is located externally of the enclosure.

FIG. 4 depicts a representative construction for a detector circuit 73. The circuit comprises a first differential amplifier 74 and a second differential amplifier 76. The two thermistors 36 and 38 are connected with inputs of amplifier 74 to form a bridge. So long as there is no trace oxygen above the trace threshold sensing level, there is no temperature differential sensed by the two thermistors 36, 38, and the bridge remains balanced. If the oxygen content exceeds the trace threshold level, the exothermic reaction occurring on pellet 40 will create a temperature rise whose effect is more pronounced on thermistor 38 than on thermistor 36 because of the intimate relationship of pellet 40 with the former thermistor. Accordingly the bridge will become unbalanced by an amount sufficient to cause the output of amplifier 74 to give a signal indicating the presence of oxygen above the trace threshold level. The accuracy of the detector circuit sensor is rendered essentially insensitive to changes in any ambient temperature variations within the enclosure by the connection of thermistor 60 to one input of amplifier 76 and the output of amplifier 74 to the other input of amplifier 76. Ambient temperature changes which otherwise might impair the accuracy of detection are thereby substantially eliminated from having influence on the ultlmate output signal which appears at the output of amplifier 76.

The sensing part 22 is physically compact, on the order of a one inch diameter and about a one and a half inch overall length from the membrane to the tip ends of the terminal pins. It can be located at any desired location within the anaerobic chamber and indeed it is possible that there could be several parts 22 placed at different locations in the large chamber. Thus the embodiment of FIGS. 2, 3, and 4 is a device well suited for anaerobic chambers.

Other embodiments are envisioned within generic principles of the invention and one of these is portrayed in FIG. 5. The detector 100 of FIG. 5 differs from the embodiment of FIGS. 2, 3, and 4 in that it does not utilize a continuous flow communication between interior of the sampling space and the anaerobic atmosphere with the enclosure. The embodiment of FIG. 5 comprises a sampling space 102 which is enclosed both volumetrically and thermally by an enclosure 104.

Enclosure 104 contains an intake port 106 and an exhaust port 108. The intake port 106 is selectively opened and closed by a suitable valve 110. An evacuation pump 112 is associated with exhaust port 108.

When a sample from the anaerobic atmosphere is to be obtained, valve 110 is opened and pump 112 operated. The sample is drawn into the sampling space via intake 106 and the sampling space is exhausted through exhaust port 108 by the action of pump 112. When the pump has been operated sufficiently long to draw a full sample into space 102, it is shut off and valve 110 is closed. Thus the sample is contained within the sampling space, and there is no communication to the exterior because both inlet and outlet are closed.

A sensor 114 is disposed to sense the temperature of the sample. The sensor is associated with an appropriate electronic circuit 116 including a memory 118 to enable the sensed ambient temperature to be stored.

A catalyst member 120 is introduced into the chamber after the ambient temperature has been stored. The introduction of the catalyst member, which may be a coiled palladium wire for example, will induce exothermic reaction of any trace oxirgen which may be present with the existing hydrogen in the atmosphere. Consequently there will be a temperature rise which can be monitored by sensor 114, and detection of a predetermined temperature rise will be indicative of oxygen above a trace threshold level.

A second temperature measurement is therefore taken in timed delay relationship to the original ambient temperature measurement a certain time after the introduction of the palladium into the chamber. A sufficient difference will indicate oxygen above the trace threshold. The unit may also include communications means 122 associated with the electronics to communicate the consequence of the sample measurement, electronically, visibly, and/or audibly. Hence FIG. 5 shows an alarm and an optional digital display associated with the electronics with the electronics calculating the difference between the two measurements and providing a corresponding signal as that difference.

Because of the time required to introduce the sample into the chamber and take the temperature measurements, the system of FIG. 5 would represent a periodic sampling occurring at perhaps one to two minute cycles. The circuitry utilized to sense temperature could be like that of FIG. 4. The enclosure may or may not include a heater for maintaining a substantially constant temperature. In this embodiment the first temperature measurement should represent ambient temperature and therefore might inherently correct for ambient temperature without a separate third transmistor as shown in FIG. 4. If some temperature correction is needed, it may be done in the electronics itself through a suitable programming. The actual sensor 114 can be the two thermistors 36, 38 connected to amplifier 74, as described in FIGS. 2, 3 and 4. The illustrated means for introducing the catalyst is intended to be merely illustrative and it can take the form of a palladium wire which is wrapped around the plunger 126 which is inserted into and removed from the sampling space via an opening in the enclosure by any suitable form of a motive means. When the palladium is disposed exterior of the sampling chamber 102 the end 128 of plunger 126 forms a stop and plug for the plunger passage.

Figure 6:
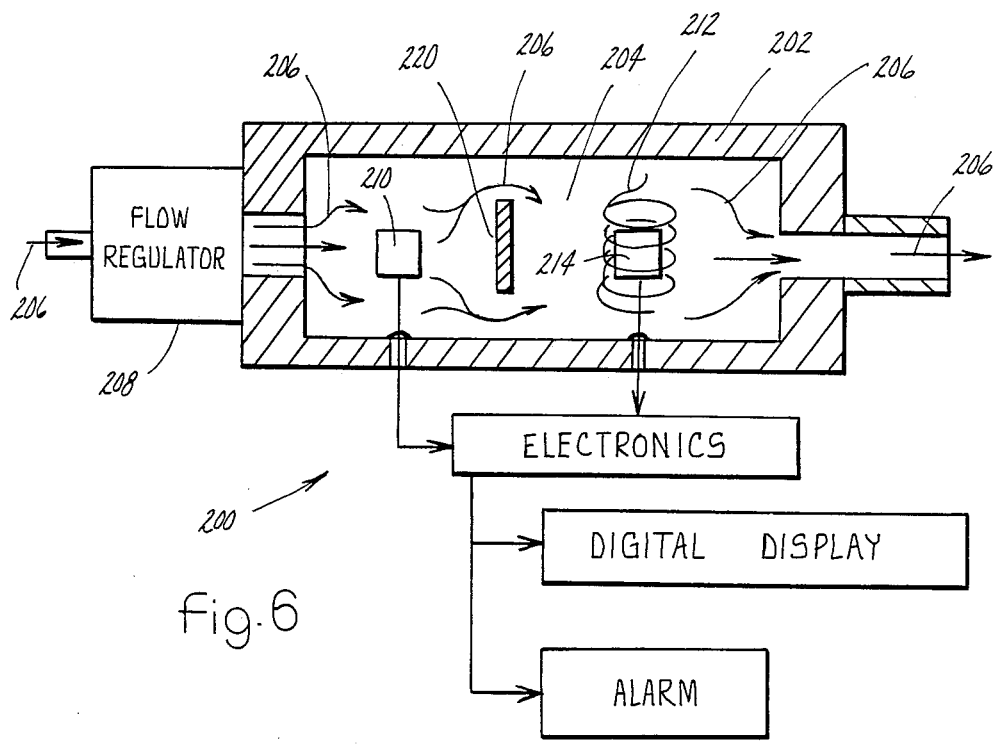
FIG. 6 is a semi-schematic view of still another embodiment of trace oxygen detector embodying principles of the present invention.

FIG. 6 illustrates another embodiment 200 which comprises an enclosure 202 for both volumetrically and thermally bounding the sampling space 204. In this version there is a continuous flow of anaerobic atmosphere through the sampling space along the path indicated by the arrows 206. The flow is induced by any suitable means and in order to regulate the flow to a substantially constant mass, a flow regulator 208 is included in the flow path.

The sample first flows past a sensor 210 which senses ambient temperature. The flow subsequently passes across a catalyst 212 which is illustrated in the form of a palladium wire suspended as a helical coil within the sampling space. A further sensor 214 is intimately associated with the catalyst. Trace oxygen which is present in the flow through the sampling chamber will react with hydrogen at the catalyst thereby giving rise to an exothermic reaction. At a sufficient level indicative of a trace oxygen exceeding the trace threshold, there will be sufficient difference detected by sensor 214 to cause the associated electronics to yield a signal indicative of oxygen above the threshold level. In this embodiment the sensor 210 corresponds to thermistor 70 of FIG. 4 to provide ambient temperature correction.

In order to minimize the influence of exothermic effects on sensor 210 it may be desirable to place a thermal shield 220 between them in a manner depicted in FIG. 6. Even though the flow is such that convective heat transfer is in the opposite direction.

FIG. 6 also shows additional communication media associated with the electronics to provide electronic, visible, audible and/or any combination thereof as indicia of the sampling results.

While a preferred embodiment of the invention has been disclosed, it will be appreciated that principles are applicable to other embodiments.

What is claimed is:

1. An anaerobic chamber for confining an anaerobic atmosphere including means for detecting the presence of oxygen above a trace level within said atmosphere comprising:

first enclosure means for defining said anaerobic chamber and means for introducing and venting gases from said first enclosure means, second enclosure means for defining a sampling space within said first enclosure means, said second enclosure means defining an aperture communicating with said anaerobic chamber, said second enclosure means having thermal characteristics which cause the temperature within said second enclosure means to change more slowly than that of said first enclosure means, said second enclosure means disposed within said first enclosure means such that all of said gases defining said anaerobic atmosphere do not pass through said second enclosure means while being introduced into or vented from said first enclosure means, a membrane extending across said aperture to thereby volumetrically confine said second enclosure means, said membrane being permeable to low molecular weight gases including oxygen and hydrogen while permitting diffusion of said anaerobic atmosphere into said second enclosure means, a catalyst disposed within said second enclosure means for promoting exothermal chemical reaction of oxygen and hydrogen passing through said membrane from said first enclosure means into said sampling space, and temperature sensing means for sensing the temperature rise within said sampling space caused by said exothermic reaction of oxygen above a trace level, said temperature sensing means including means to compensate for ambient temperature variations.

2. Means for sensing the presence of a trace level of oxygen in an anaerobic atmosphere as set forth in claim 1 in which said catalyst comprises a pellet disposed on said one temperature device.

3. Means for sensing the presence of a trace level of oxygen in an anaerobic atmosphere as set forth in claim 1 which said temperature sensing means comprises two temperature sensing devices disposed within said sampling space, one of which is disposed physically closer to said catalyst than is said other temperature sensing device so as to have a higher degree of thermal sensitivity to exothermic reaction occurring at said catalyst than is the other temperature sensing device.

4. Means for sensing the presence of a trace level of oxygen in an anaerobic atmosphere as set forth in claim 3 including a third temperature sensing device disposed exteriorly of said sampling space for sensing ambient temperature within the anaerobic atmosphere.

5. Means for sensing the presence of a trace level of oxygen in an anaerobic atmosphere as set forth in claim 4 in which said one and said other temperature sensing devices are connected as input in a bridge circuit and the output of said bridge circuit is connected with said third temperature sensing device in a further bridge circuit which provides an output signal indicating whether oxygen is above or below the trace level.

6. Means for sensing the presence of a trace level of oxygen in an anaerobic atmosphere as set forth in claim 4 in which said first and second temperature sensing devices are connected as inputs to an amplifier to form a bridge and the output of the amplifier is connected as an input to a further amplifier and the third temperature sensing device is connected to another input of the second amplifier so that the further amplifier, the third temperature sensing device, and the output of the first amplifier form a further bridge.

7. Means for sensing the presence of a trace level, of oxygen in an anaerobic atmosphere as set forth in claim 1 in which said second enclosure includes a thermal conductor mass constructed and arranged to present sufficiently large thermal inertia to enable heat of exothermic reactions to be retained within the sampling chamber for sufficient length of time to enable detection of oxygen above the trace level.

8. Means for sensing the presence of a trace level of oxygen in an anaerobic atmosphere as set forth in claim 7 including a heating system for maintaining said thermal conductor mass at a constant temperature.

* * * * *